(12) United States Patent
Cluckers et al.

(10) Patent No.: US 10,482,214 B2
(45) Date of Patent: Nov. 19, 2019

(54) METHODS AND APPARATUSES FOR DESIGNING FOOTWEAR

(71) Applicant: RSPRINT NV, Beringen (BE)

(72) Inventors: Tom Cluckers, Kuringen (BE); Jean-Pierre Wilssens, Beveren (BE)

(73) Assignee: RSPRINT NV, Beringen (BE)

( * ) Notice: Subject to any disclaimer, the term of this patent is extended or adjusted under 35 U.S.C. 154(b) by 251 days.

(21) Appl. No.: 15/347,055

(22) Filed: Nov. 9, 2016

(65) Prior Publication Data
US 2017/0068774 A1    Mar. 9, 2017

Related U.S. Application Data

(63) Continuation-in-part of application No. PCT/EP2015/060161, filed on May 8, 2015, and a
(Continued)

(51) Int. Cl.
*A43B 7/14* (2006.01)
*A61B 5/103* (2006.01)
(Continued)

(52) U.S. Cl.
CPC .......... *G06F 17/5086* (2013.01); *A43B 7/147* (2013.01); *A61B 5/1036* (2013.01);
(Continued)

(58) Field of Classification Search
CPC .. G06F 17/5086; G06F 17/50; G06F 2217/32; A61B 5/743; A61B 5/1036;
(Continued)

(56) References Cited

U.S. PATENT DOCUMENTS 5,231,776 A * 8/1993 Wagner ............... A43B 19/005
36/1
8,005,558 B2    8/2011 Waatti et al.
(Continued)

FOREIGN PATENT DOCUMENTS

CN    101388119 A    3/2009
EP    1980224 A2    10/2008
(Continued)

OTHER PUBLICATIONS

International Search Report—PCT EP/2015/060162—ISA/EPO—dated Jul. 31, 2015.
(Continued)

*Primary Examiner* — Juan C Ochoa
(74) *Attorney, Agent, or Firm* — Patterson + Sheridan, LLP

(57) ABSTRACT

Methods and apparatuses for designing custom footwear are disclosed. An apparatus for designing custom footwear may include a data collection system, a data processing system, and a manufacturing system, where the manufacturing system includes an additive manufacturing device. A method for designing custom footwear may comprise receiving user-specific data, generating a user model, identifying issues in the user model, determining corrective features, generating a custom footwear model, and manufacturing the custom footwear.

12 Claims, 9 Drawing Sheets

Related U.S. Application Data continuation-in-part of application No. PCT/EP2015/060162, filed on May 8, 2015.

(60) Provisional application No. 61/991,318, filed on May 9, 2014, provisional application No. 61/991,298, filed on May 9, 2014.

(51) Int. Cl.

| | | |
|---|---|---|
| *A61B 5/11* | (2006.01) | |
| *A61B 5/00* | (2006.01) | |
| *B33Y 80/00* | (2015.01) | |
| *A43D 1/02* | (2006.01) | |
| *A43B 13/14* | (2006.01) | |
| *A43B 17/00* | (2006.01) | |
| *G06F 17/50* | (2006.01) | |
| *A43B 7/24* | (2006.01) | |

(52) U.S. Cl.
CPC .............. *A61B 5/112* (2013.01); *A61B 5/743* (2013.01); *B33Y 80/00* (2014.12); *G06F 17/50* (2013.01); *A43B 7/141* (2013.01); *A43B 7/24* (2013.01); *A43B 13/14* (2013.01); *A43B 17/00* (2013.01); *A43D 1/02* (2013.01); *A43D 1/022* (2013.01); *A43D 1/025* (2013.01); *A43D 2200/60* (2013.01); *G06F 2217/32* (2013.01)

(58) Field of Classification Search
CPC .... A61B 5/112; A43D 1/025; A43D 2200/60; A43B 17/00; A43B 7/147; A43B 13/14; A43B 7/24
USPC .......................................................... 703/1
See application file for complete search history.

(56) References Cited

U.S. PATENT DOCUMENTS

| | | | | |
|---|---|---|---|---|
| 8,036,768 | B2* | 10/2011 | Lowe ................... | A43D 1/02 |
| | | | | 12/146 M |
| 8,152,744 | B2* | 4/2012 | Mukumoto ........... | A43B 7/28 |
| | | | | 600/587 |
| 9,201,988 | B2* | 12/2015 | Stanhope ............. | G01B 5/008 |
| 2002/0138923 | A1 | 10/2002 | Shaffeeullah | |
| 2004/0133431 | A1* | 7/2004 | Udiljak ................ | A43B 7/141 |
| | | | | 705/26.1 |
| 2005/0203712 | A1 | 9/2005 | Lowe | |
| 2008/0292179 | A1* | 11/2008 | Busch .................. | A43B 17/00 |
| | | | | 382/154 |
| 2009/0073162 | A1 | 3/2009 | Waatti et al. | |
| 2015/0006119 | A1 | 1/2015 | Arayama et al. | |
| 2016/0374428 | A1* | 12/2016 | Kormann ............. | A43B 13/186 |
| | | | | 36/28 |
| 2016/0374431 | A1* | 12/2016 | Tow .................... | A43B 17/003 |
| | | | | 36/43 |
| 2017/0038767 | A1* | 2/2017 | Cluckers ............. | G06F 17/50 |
| 2018/0315206 | A1* | 11/2018 | Maes ................... | G06T 7/55 |

FOREIGN PATENT DOCUMENTS

| | | |
|---|---|---|
| JP | 2005-192744 A | 7/2005 |
| JP | 2007-526028 A | 9/2007 |
| WO | 2014/042094 A1 | 3/2014 |

OTHER PUBLICATIONS

Office Action dated Oct. 31, 2018 for Chinese Application No. 201580024140.5, filed May 8, 2015.

* cited by examiner

FIG. 3B

METHODS AND APPARATUSES FOR DESIGNING FOOTWEAR

CLAIM OF PRIORITY UNDER 35 U.S.C. § 119

This application is a continuation-in-part of PCT/EP2015/060162, filed May 8, 2015, which claims priority to U.S. Patent Application Ser. No. 61/991,298, filed May 9, 2014. This application is also a continuation-in-part of PCT/EP2015/060161, filed May 8, 2015, which claims priority to U.S. Provisional Patent Application No. 61/991,318, filed May 9, 2014, all of which are herein incorporated by reference in their entirety.

FIELD OF THE INVENTION

This application relates to the field of footwear, in particular to methods and apparatuses for designing custom footwear.

Traditional footwear is not customized for a user. Rather, the footwear is designed based on general characteristics that apply to most feet, most of the time. As a result, footwear is often not comfortable to users and/or not capable of correcting or preventing problematic foot related conditions.

Footwear inserts (e.g. insoles) have been used in an effort to correct various issues related to the foot. Unfortunately, in most cases, the footwear inserts are no more suited to a user's foot than the original footwear. Consequently, "custom" footwear inserts have been developed in order to try and correct or prevent issues while taking into account, to some extent at least, a user's actual foot.

Unfortunately, custom footwear inserts have been mostly limited to custom insoles meant to be used in otherwise non-custom footwear. Because other aspects of the non-custom footwear, such as, for example, the midsole and outsole, are not customized for a user, the effectiveness of the custom footwear inserts has been limited.

Further, the design of custom footwear inserts is often a manual, time-consuming, error-prone, and expensive operation. As such, large-scale manufacturing of such custom footwear inserts has been problematic since, by definition, each footwear insert is custom. These factors and others have limited the availability and effectiveness of custom footwear and increased their cost.

Accordingly, what is needed are improved methods and apparatuses for designing and manufacturing custom footwear.

SUMMARY

This application describes methods and apparatuses for designing custom footwear, and in particular, custom footwear portions, such as: insoles, midsoles, and outsoles.

In one embodiment, a method of designing a custom footwear model based on a user model, comprises: receiving user data associated with a user; generating a user model based on the received user data; determining one or more corrective features based on the user model; and generate a custom footwear model comprising a determined corrective feature.

The method may further comprise creating a footwear part based on the custom footwear model, wherein the footwear part is created by an additive manufacturing technique.

In some embodiments of the method, the user data includes one or more of: foot pressure data, gait data, body data, or image data.

In some embodiments of the method, determining one or more corrective features is additionally based on statistical data.

In some embodiments of the method, the statistical data comprises a statistical shape model.

In some embodiments of the method, the footwear part is one of an insole, a midsole, or an outsole.

In some embodiments of the method, the custom footwear model comprises at least one of a bend line pattern, an altered thickness area, or a cellular structure.

In some embodiments of the method, the footwear part comprises at least one of a bend line pattern, an altered thickness area, or a cellular structure.

In some embodiments of the method, the footwear part is configured to alter a biomechanical action of the user's foot.

In some embodiments of the method, the footwear part is configured to improve a static weight distribution of a user's foot.

In another embodiment, an apparatus configured to design a footwear part comprises: a data store comprising footwear template models and executable software; a sensor configured to create user data; and a processor in data communication with the data store and the sensor, wherein the processor is configured to execute the software and cause the apparatus to: receive user data associated with a user; generate a user model based on the received user data; determine one or more corrective features based on the user model; and generate a custom footwear model comprising a determined corrective feature.

The processor may further be configured to execute the software and further cause the apparatus to: create a footwear part based on the custom footwear model, wherein the footwear part is created by an additive manufacturing technique.

In some embodiments of the apparatus, the user data includes one or more of: foot pressure data, gait data, body data, or image data.

In some embodiments of the apparatus, the processor is configured to execute the software and further cause the apparatus to: determine the one or more corrective features based on statistical data.

In some embodiments of the apparatus, the statistical data comprises a statistical shape model.

In some embodiments of the apparatus, the footwear part is one of an insole, a midsole, or an outsole.

In some embodiments of the apparatus, the custom footwear model comprises at least one of a bend line pattern, an altered thickness area, or a cellular structure.

In some embodiments of the apparatus, the footwear part comprises at least one of a bend line pattern, an altered thickness area, or a cellular structure.

In some embodiments of the apparatus, the footwear part is configured to alter a biomechanical action of the user's foot.

In some embodiments of the apparatus, the footwear part is configured to improve a static weight distribution of a user's foot.

BRIEF DESCRIPTION OF THE DRAWINGS

FIG. 3B depicts a graphical user interface of an exemplary footwear design component.

DETAILED DESCRIPTION OF CERTAIN INVENTIVE EMBODIMENTS

Figure 1:
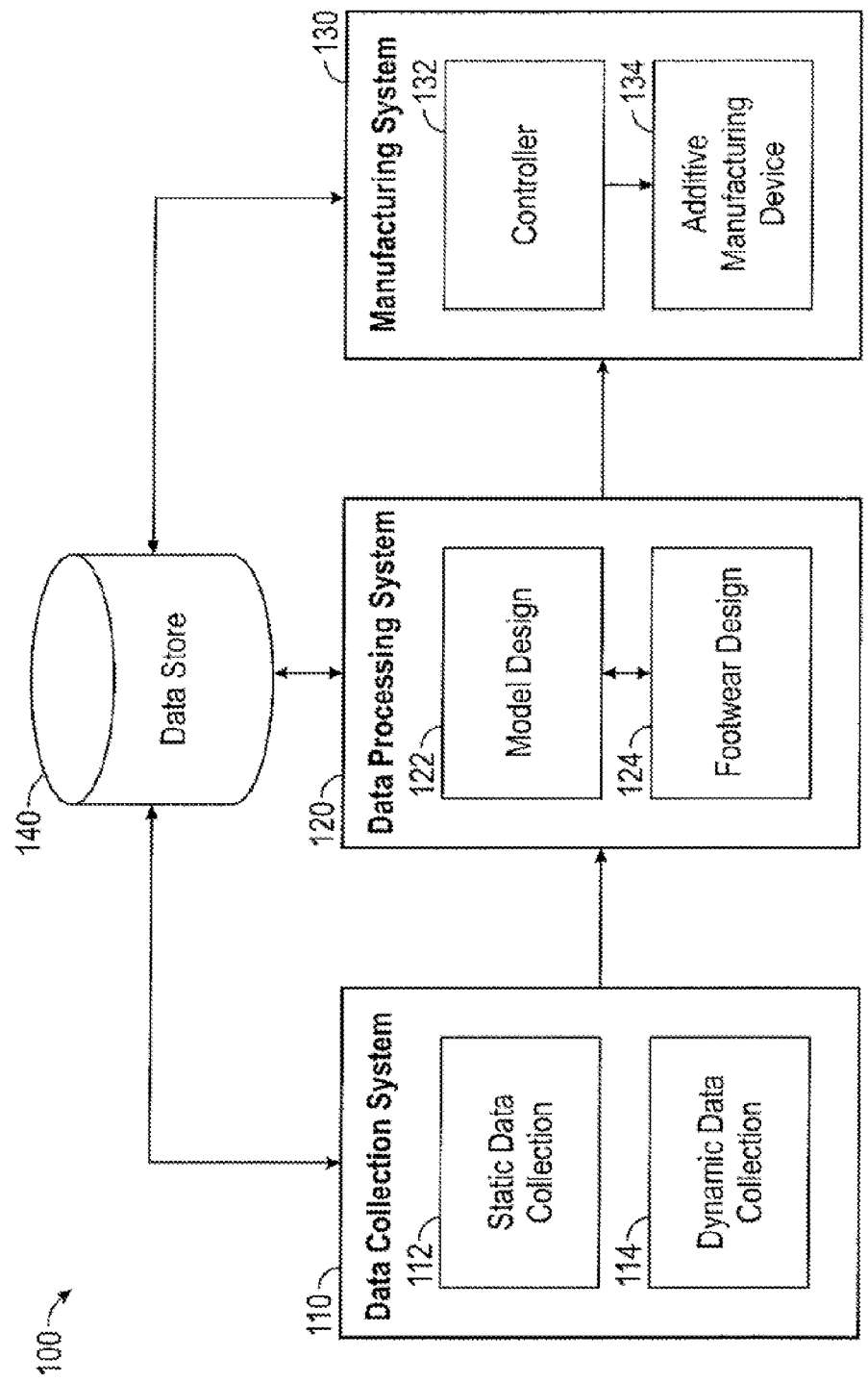
FIG. 1 depicts an embodiment of a custom footwear system.

Custom footwear may be beneficial for the treatment of a variety of known conditions related to the foot. For example, pronation in the foot (i.e. inward roll of the foot while standing, walking and running) may lead to swelling and Achilles tendon issues. To treat the pronation, custom footwear may be designed to correct or improve the static and dynamic pressures on the foot. For example, the custom footwear may correct support under the medial arch of the foot, and may reduce the ability of the footwear to bend in certain directions.

As another example, a bunion may be treated with custom footwear that reduces medial load and provides customized support for the hallux (i.e. big toe). Other conditions may also be treated using custom footwear, such as: plantar fasciitis, arthritis, poor circulation, metatarsalgia, patellofemoral knee pain, shin splints, Achilles tendonitis, repetitive strain injuries and others as are known by persons of skill in the art.

In addition to treating existing, adverse foot conditions, custom footwear may also help to prevent injuries and the onset of foot conditions. For example, custom footwear may reduce stress related injuries to the foot, ankle, leg, knee, back, etc. by better distributing the weight during the impact of footfalls, or by altering the way a foot falls and rotates during dynamic movements. Similarly, custom footwear may prevent movement in certain directions (such as rolling ankle movement) while promoting movement in other directions (such as rolling of the forefoot during transitional movements.

Moreover, custom footwear may improve biomechanical performance (e.g. for athletes). For example, custom footwear may alter the angle of impact of a foot during dynamic activities such as running, which may in-turn increase the overall speed of the runner. Many other benefits of custom footwear exist, as are known by persons of skill in the art.

Custom footwear may be designed using data regarding a particular user's physical characteristics or attributes—so called "static" user data. For example, a user's foot size and static foot pressure (e.g. when standing) may be measured.

Custom footwear may also be designed using dynamic user data, such as dynamic foot pressure measurements. For example, the dynamic pressures on a user's foot may be measured during dynamic foot activities, such as: running, walking, jumping, landing, pivoting, rolling, rocking, etc. Virtually any functional biomechanical measurements may be used during the design of custom footwear.

Custom footwear may also be designed using non-user-specific data, such as a statistical population data. For example, the average shape of a foot of a certain size may be statistically determined, or otherwise available from existing statistical datasets. Further, the statistical averages for these and other physical foot characteristics may have associated statistical parameters, such as distributions, standard deviations, variances, and others as are known in the art. In this way, knowing a single foot characteristic associated with a user, such as a shoe size, may enable the use of many associated statistical foot characteristics (e.g. shape, size, etc.).

Ultimately, as described in more detail below, the aforementioned data types and others may be used to create custom footwear that accounts for: user-specific anatomical features, user-specific orthopedic needs, user-specific treatment needs, user-specific performance needs, and others as are known by persons of skill in the art.

Static User-Specific Data

Static user-specific data may be used in the design of custom footwear. Different types of static user-specific data can be generated by different methods.

For example, basic user data such as: gender, height, and weight may be used for the design of custom footwear. Some basic user data may be objective data (e.g. height and weight), while other basic user data may be subjective (e.g. activity level and user preferences).

Static user-specific data may be body-part-specific. For example, data related to a particular user's foot may include: foot length, foot width, arch height, arch location, foot shape, footprint, shoe size, flexion or extension of foot in various directions, inversion and eversion of the foot, strength of various foot muscles, bone alignment, pronation, supination, and other characteristics as are known by persons of skill in the art. In some instances, physical characteristics may be determined using manual physical measurements (e.g. a measuring tape), while others may be determined by digital measurement systems (e.g. a digital scale).

Given the complexity of the shape and composition of various body parts, such as the foot, more precise data capture methods may be advantageous.

For example, user-specific data may be generated using one or more image sensors, such as live or still cameras. Various types of cameras can be used, including: traditional digital cameras with a single image sensor or stereoscopic cameras with two or more image sensors. Traditional digital cameras, including mobile device cameras, may be used by taking a plurality of images of an object, such as a body part, from different angles in order to infer depth and 3D structure. The plurality of images of the body part, such as a foot (or other anatomical features such as the ankle, calf, etc.), may be analyzed by, for example, a computer system, in order to determine three-dimensional (3D), user-specific data, such as a 3D model.

For example, U.S. Pat. No. 8,126,261, entitled "3D Face Reconstruction from 2D Images", which is incorporated by reference in its entirety herein, discloses methods for determining 3D models of, e.g., a face, from a plurality of two-dimensional (2D) images. Likewise, PCT Patent Publication WO 2012/129252, entitled "Digital 3D Camera Using Periodic Illumination," which is incorporated by reference in its entirety herein, discloses methods of using a digital camera and projected light patterns to determine 3D models using 2D image data. Additionally, two or more cameras may be used simultaneously to generate 3D user-specific data. For example, U.S. Pat. No. 8,532,368, entitled "Method and Apparatus for Producing 3D Model of An Environment," which is incorporated herein by reference in its entirety, describes methods of using a mobile stereo camera system to determine 3D models. Accordingly, image sensors may be used with the aforementioned methods and others as are known in the art in order to capture 2D user-specific data and to build user-specific 3D models based on the 2D data.

In some cases, mobile devices (e.g. smartphones and tablets) may include stereoscopic image sensors, which may be referred to as "3D cameras." Such devices may have the ability to capture image data and create 3D data or a 3D model without the need for additional processing by an independent processing system.

Additionally, more advanced camera systems, such as the "Kinect," available from Microsoft Corporation (Redmond, Wash., USA) provide image data including depth information. Similarly, purpose-built 3D scanners using image sensors, like the "Gotcha" 3Dscanner of 4DDynamics (Antwerp, Belgium) or MakerBot® Digitizer™ (New York, N.Y., USA) may be used.

An advantage of using an image capture device, such as one or more cameras, for determining user-specific data is that such devices are typically digital, portable, and relatively inexpensive. As such, systems for designing custom footwear may be wholly or partially (e.g. the imaging system) portable. Portability of the system increases the ability to use such a system in different contexts.

Other devices may be used to generate 3D user-specific data. For example, optical scanners, laser-based scanners, and other scanning systems as are known by persons of skill in the art may be used to scan a body part, such as a foot, and to create a 3D model associated with the scanned body part. An advantage of, for example, laser-based or optical scanning systems is that they may create very accurate 3D models of the object being scanned. However, such scanning systems may be less portable and more costly than an image-based modeling system, such as those described above.

Medical imaging techniques may also be used to generate 2D and 3D user-specific data. For example, X-ray scans, computed tomography (CT) scans, positron emission tomography (PET) scans, magnetic resonance imaging (MM), ultrasound scans, and other medical imaging techniques as known by those of skill in the art may be used to create 2D and 3D user specific data, which may in-turn be used to create a 2D or 3D model of a body part, such as a foot. In particular, certain types of medical imaging may also provide additional detail regarding internal anatomical features and functions, such as bone structures, bone alignment, muscle and ligament placement, cartilage placement, and others as are known in the art. The design of custom footwear may beneficially account for such features.

Sensors may also be used to determine user-specific data. For example, a pressure sensitive pad may record the distribution of pressures associated with a user's footprint. That is, a user may stand on a pressure sensitive pad in order to generate a plurality of pressure reading associated with the user's static footprint.

In some instances, various forms of measurement, imaging and sensing may be performed on a cast, mold, or other impression of a user's body part, such as a foot mold. This capability allows for the design of custom footwear without the need for a user to be collocated with, for example, the scanning equipment. In other instances, a user may generate data, such as 2D or 3D image data, using his or her own equipment, such as a camera-equipped mobile phone or video camera, and then provide that data to a data processing system meant to design custom footwear for that user. In this way, the user need not be collocated with other aspects of a custom footwear design system. For example, the user may provide basic user data (e.g. height, weight, and preference data) along with a plurality of self-generated 2D image data to a remote service that uses the data to design and manufacture custom footwear for that user.

Generally speaking, the aforementioned methods of generating static user-specific data may be used to create detailed 2D or 3D models of a user's body part, such as a foot. Those models may in-turn be used to design custom footwear for the user. To that end, computer-aided design (CAD) or computer-aided manufacturing (CAM) software, such as software commercially available by Materialise USA (Plymouth, Mich., USA) may be used to process the userspecific data and to create custom footwear designs.

Dynamic User-Specific Data

Custom footwear may also be designed using dynamic user-specific data. Dynamic user-specific data includes data collected regarding dynamic user movements, such as: running, walking, jumping, landing, pivoting, rolling, rocking, etc.

One means of measuring dynamic user-specific data is a pressure sensitive mat or pad that is configured to measure pressure data over time and to provide that data to, for example, a processing system. Such pressure sensitive pads may be relatively large, such that they can measure more than one foot at once during user movements. Additionally, pressure sensitive pads of sufficient size may be able to measure characteristics such as: stride, gait, alignment, footfall, foot rotation, and others as are known by persons of skill in the art.

Systems that measure the dynamic pressure distribution on a foot are described, for example, in European patent applications EP0970657A1 and EP1127541A1, each of which is incorporated by reference in its entirety. Based on the measurement of dynamic pressures on a foot during movement, assumptions can be made about the movement of various parts of the foot. Ultimately, custom footwear may be designed based on the dynamic pressure measurements.

Pressure sensitive devices may be used in conjunction with other dynamic data capture devices, such as user-wearable force sensors, motion capture sensors, image sensors, and the like. Force sensors, for example, may be attached to a user to measure force as the user moves dynamically. In some instances, mobile devices including motion sensitive sensors may be used to gather motion data to be analyzed. Thus, as described above, a user may use his or her own mobile device not only to capture static user data (such basic user data and still images), but also to capture dynamic user data, such as force and motion data. In some instances, a user may collect all the data necessary for a custom footwear design using his or her own mobile device.

Motion capture systems may be used to capture and analyze dynamic user data. For example, systems using computer-identifiable targets attached to a user and a monitoring system may track the targets in order to generate dynamic user data.

Dynamic data measurements may be combined. For example, pressure sensitive pads and/or motion sensors may be used alongside video capture equipment so that the dynamic data can be compared with video footage of a user in action. For example, a high-speed camera may record the movement of a user's body part, such as a foot, while pressure sensitive sensors capture data regarding the foot's movement, impacts, etc.

Statistical Body Part Data

Custom footwear may also be designed using statistical body part data such as population data. For example, a particular size of shoe may be associated with several characteristics that are statistically predictable based on analyzing population data. As mentioned above, a particular size of shoe may be associated with statistical distributions regarding the length and width of an "average" foot of that size, as well as placement of various anatomical features, such as toes, heel, arch, etc. for a foot of that size.

In some instances, a statistical shape model (SSM) may be constructed based on a plurality of user-specific 2D or 3D body part data. Statistical shape models can be used, for example, to analyze the shape of a user's body part, or to create a model of the user's body part in order to design custom footwear. Such statistical shape models may be particularly useful where the only user-specific data available is incomplete or inaccurate. Additionally, a statistical shape model of a body part, such as a foot, may be used to provide automated analysis of 2D or 3D image data of that body part.

User Model

A user model may be generated based on one or more of static user-specific data, dynamic user-specific data, statistical data, or other data as described herein. In some instances, the user model may be a 2D or 3D model of a user's body part, such as a user's foot. In some instances, the user model may include graphical information, such as a depiction of a user's body part in 2D or 3D, or may instead be a data model including various attributes or characteristics regarding the user. In some instances, the user model includes both graphical data and attribute data within the same model. For example, a user model may include a visual representation of a user's body part based on imaging data as well as pressure data associated with various points on the visual representation based on dynamic user-specific data.

In some instances, such as where little if any reliable user-specific data is received, the user model may be generated based primarily on statistical data or on a template, or on both. For example, the user model may be supplemented with static or dynamic data, such as pressure data. This data may be enhance the model so that appropriate custom footwear can be designed for the user. Footwear Portions
[0069] Custom footwear may comprise several individual footwear portions, such as, for example: a body, an insole, a midsole, and an outsole.

The body may be the portion of the footwear (such as a shoe) that surrounds the sides and top of a user's foot. The body may comprise portions, such as a heel support, ankle support, webbing, laces, straps, tongue, and other structures as are known in the art. In some cases the body may comprise two or more portions that are selectively bound by a user using, for example, laces or straps.

An insole may be the inner portion of footwear (such as a shoe) that directly contacts the bottom (and to some extent side) of a user's foot. A custom insole may be a fixed (i.e. permanent) portion of a shoe, or a removable portion of a shoe in different instances.

A midsole may be a footwear portion between the insole and the outsole, which, in some instances, is primarily a shock-absorbing portion. In some instances, the midsole may be designed to be primarily responsible for supporting a substantial portion of the weight of a user as well as providing shock absorbing properties for the footwear while in use. In other instances, the midsole may be designed to enhance the effectiveness of features found in the insole and/or outsole.

The outsole may be the outer-most portion of footwear, and may be designed to interface with the ground. In some instances, the outsole is alternatively known as a tread. The outsole may be designed with, for example, structures and/or textures for providing grip to the footwear on a variety of surfaces. Additionally, the outsole may be designed to protect a user's foot from puncture or other harmful intrusion. As with above, the outsole may additionally be designed to enhance the effectiveness of features found in the midsole.

In some instances, footwear (such as a shoe) may include one or more of the aforementioned portions. Different combinations of these footwear portions are envisioned. For example, particular footwear may have a body, an outsole, and an insole, but lack a midsole. In some instances, one or more of the body, insole, midsole, and outsole are permanently attached to each other. For example, while being designed separately, and potentially comprising different materials, a body, an insole, a midsole, and an outsole may nonetheless be manufactured as integral footwear.

In some instances, one or more of the body, insole, midsole, and outsole are custom footwear portions designed at least in part based on the various types of data described above. In some instances, one or more of the aforementioned footwear portions may comprise one or more materials and/or structures or corrective features. For example, a midsole may comprise various 3D structures meant to absorb shock while reducing the overall weight of the footwear.

Corrective Features in Footwear

Custom footwear may include one or more corrective features specifically designed to affect the fit and/or behavior of the footwear when worn and used by a user.

In some embodiments, corrective features are meant to correct anatomical or biomechanical problems with a user's foot. For example, a user may have a relatively high arch, which creates support issues with regular footwear. As such, custom footwear may include a custom footwear portion, such as an insole, that adds support underneath the high arch in order to better distribute the user's weight in the footwear.

In some embodiments, corrective features are meant to prevent injury rather than to correct an injury or anatomical problem. For example, dynamic data can be used to determine the balance of a user's foot during movement (e.g. when running). The determined balance may be compared to optimal balance sequences, which may be derived from dynamic or statistical data characterizing user, such as athletes, who perform at a high level without injuries over long periods of time. Thus, corrective structures may be designed to promote better foot balance during movement in order to prevent injury.

In further embodiments, corrective features are meant to improve performance rather than to correct an existing or potential problem. For example, it has been shown that characteristics related to initial foot contact during running are related to running speed in athletes. With this in mind, dynamic data may be collected to determine characteristics of a user's initial foot contact during running, such as:

landing zone (e.g. heel, mid-foot, fore-foot); the ratio between the respective forces acting on the median part and the lateral part of the foot; the maximum forces on the landing; the speed of the unreeling of the foot; and others as are known in the art. Based on these determination, a custom footwear portion, such as a midsole or outsole, can be configured to alter the user's initial foot contact when running to improve running speed and/or efficiency.

Corrective features may, for example, comprise areas of reduced or increased thickness in a footwear portion. For example, a custom insole may have an area near the arch with increased thickness to provide additional support to the arch.

Corrective features may also comprise bending lines, ribs, cuts, striations or other patterns that enhance or inhibit bending of a footwear portion in certain directions. The number, thickness, direction, and relative proximity of such corrective features may influence the propensity of the footwear portion to bend in certain directions. For example, an outsole may include ribs and cuts in a particular direction in order to enhance the tendency for the outsole to bend in a designed direction and to counteract the tendency to bend in an undesirable direction.

Corrective features may also comprise relatively simple or relatively complex microstructures. Examples of microstructures include, for example, beams, lattices, regular 3D grids, regular or irregular open or closed cell structures, foam or sponge-like formations, trusses, springs, shocks, triclinic, monoclinic, orthorhombic, hexagonal, trigonal, tetragonal, or cubic structures, and others as are known in the art. Microstructures may influence the characteristics of footwear portions, such as the mechanical behavior of the footwear portions. Further, microstructures may influence other characteristics of footwear portions, such as: elasticity, viscoelasticity, rigidity, abrasion resistance and density. Notably, the prefix "micro" in "microstructure" primarily refers to the ability to customize the structure at a very small level. It does not limit the size of the microstructures as a whole. Indeed, structures comprising microstructures may be built to any size or shape.

In addition to the form of the microstructure, the position and size of the structure (or its component parts) may influence characteristics of footwear.

Additionally, characteristics of connection points between microstructures may also influence characteristics of footwear. For example, the thickness of a connection point may affect the mechanical properties of a particular footwear portion. In some instances, connection points can be, for example, selectively thickened or thinned in order to affect the way the footwear portion reacts to different loads in different directions.

In some instances, corrective features may be layered or combined to give a footwear portion more complex characteristics. For example, in addition to varying the thickness of a certain footwear portion, the individual layers making up the thickness of that portion may include unique corrective features, such as microstructures or others as described above.

In some instances, the corrective features may be on the surface of a footwear portion. For example, surface features such as textures, patterns, lines, or others as described above may be used to provide more grip, more feel, more comfort, etc. to a user of the custom footwear.

In some instances, one or more of the aforementioned corrective features may be arranged in zones associated with footwear portions. Such zones may be configured to influence different mechanical properties of the footwear in different areas. In some instances, an entire footwear portion may be a zone, and in other instances a footwear portion (e.g. an insole) may include one or more zones. In some instances, a zone may comprise a single corrective feature, such as a microstructure.

In sum, the selection, arrangement and physical characteristics of different corrective features in footwear may be used to correct or counteract a user's biomechanical issues, prevent injuries, and/or promote increased performance.

Additive Manufacturing

Custom footwear can be manufactured using additive manufacturing techniques. Many methods of additive manufacturing are known in the art, such as: Stereolithography (SLA), Selective Laser Sintering (SLS), Selective Laser Melting (SLM) and Fused Deposition Modeling (FDM), among others.

Stereolithography (SLA) is an additive manufacturing technique used for "printing" 3D objects one layer at a time. An SLA apparatus may employ, for example, a laser to cure a photo-reactive substance with emitted radiation. In some embodiments, the SLA apparatus directs the laser across a surface of a photo-reactive substance, such as, for example, a curable photopolymer ("resin"), in order to build an object one layer at a time. For each layer, the laser beam traces a cross-section of the object on the surface of the liquid resin, which cures and solidifies the cross-section and joins it to the layer below. After a layer has been completed, the SLA apparatus lowers a manufacturing platform by a distance equal to the thickness of a single layer and then deposits a new surface of uncured resin (or like photo-reactive material) on the previous layer. On this surface, a new pattern is traced thereby forming a new layer. By repeating this process one layer at a time, a complete 3D part may be formed.

Selective laser sintering (SLS) is another additive manufacturing technique used for 3D printing objects. SLS apparatuses often use a high-powered laser (e.g. a carbon dioxide laser) to "sinter" (i.e. fuse) small particles of plastic, metal, ceramic, or glass powders into a 3D object. Similar to SLA, the SLS apparatus may use a laser to scan cross-sections on the surface of a powder bed in accordance with a CAD design. Also similar to SLA, the SLS apparatus may lower a manufacturing platform by one layer thickness after a layer has been completed and add a new layer of material in order that a new layer can be formed. In some embodiments, an SLS apparatus may preheat the powder in order to make it easier for the laser to raise the temperature during the sintering process.

Selective Laser Melting (SLM) is yet another additive manufacturing technique used for 3D printing objects. Like SLS, an SLM apparatus typically uses a high-powered laser to selectively melt thin layers of metal powder to form solid metal objects. While similar, SLM differs from SLS because it typically uses materials with much higher melting points. When constructing objects using SLM, thin layers of metal powder may be distributed using various coating mechanisms. Like SLA and SLS, a manufacturing surface moves up and down to allow layers to be formed individually.

Fused Deposition Modeling (FDM) is another additive manufacturing technique wherein a 3D object is produced by extruding small beads of, for example, thermoplastic material from an extrusion nozzle to form layers. In a typical arrangement, the extrusion nozzle is heated to melt the raw material as it is extruded. The raw material then hardens immediately after extrusion from a nozzle. The extrusion nozzle can be moved in one or more dimensions by way of appropriate machinery. Similar to the aforementioned additive manufacturing techniques, the extrusion nozzle follows a path controlled by CAD or CAM software. Also similar, the part is built from the bottom up, one layer at a time.

Objects may be formed by additive manufacturing apparatus using various materials, such as: polypropylene, thermoplastic polyurethane, polyurethane, acrylonitrile butadiene styrene (ABS), polycarbonate (PC), PC-ABS, PLA, polystyrene, lignin, polyamide, polyamide with additives such as glass or metal particles, methyl methacrylate-acrylonitrilebutadiene-styrene copolymer, resorbable materials such as polymer-ceramic composites, and other similar suitable materials. In some embodiments, commercially available materials may be utilized. These materials may include: DSM Somos® series of materials 7100, 8100, 9100, 9420, 10100, 11100, 12110, 14120 and 15100 from DSM Somos; ABSplus-P430, ABSi, ABS-ESDI, ABS-M30, ABS-M30i, PC-ABS, PC-ISO, PC, ULTEM 9085, PPSF and PPSU materials from Stratasys; Accura Plastic, DuraForm, CastForm, Laserform and VisiJet line of materials from 3-Systems; Aluminium, CobaltChrome and Stainless Steel materials; Maranging Steel; Nickel Alloy; Titanium; the PA line of materials, PrimeCast and PrimePart materials and Alumide and CarbonMide from EOS GmbH.

Custom footwear, including custom footwear portions, may be manufactured using additive manufacturing techniques. Advantageously, an additive manufacturing apparatus may "3D print" an entire footwear portion or an entire piece of footwear in a single, integral workpiece. For example, rather than manufacturing insoles, midsoles and outsoles separately, an additive manufacturing device may create a custom footwear portion layer-by-layer with non-homogeneous corrective features (e.g. microstructures) in each individual layer. Thus, 3D printing may provide a much higher degree of customization of footwear as compared to traditional manufacturing techniques.

Further, 3D printing custom footwear may advantageously reduce the number of materials and individual pieces that need to be manufactured in order to arrive at a desired footwear design. Moreover, additive manufacturing techniques may take advantage of a wider range of materials for creating custom footwear as compared to traditional manufacturing techniques.

In some instances, additive manufacturing techniques may improve traditional manufacturing steps. For example, footwear portions may include surface textures, patterns, structures, etc., which may be useful for traditional manufacturing steps such as gluing, fusing, or otherwise fastening portions together. In some instances, the surface textures may be created by microstructures. As another example, an additively manufactured footwear portion may be finished with a manufacturing layer that has a high porosity and/or a particular texture in order to improve the joining of that portion with another footwear portion by glue or other fastening means.

Description of Certain Exemplary Embodiments

FIG. 1 depicts an embodiment of a custom footwear system 100. In the depicted embodiment, the custom footwear system 100 comprises a data collection system 110, a data processing system 120, a manufacturing system 130, and a data store 140.

Data collection system 110 collects data regarding a particular user, such as information regarding a user's foot or feet. Data collection system 110 may comprise a static data collection component 112 as well as a dynamic data collection component 114.

Static data collection component 112 collects static user-specific data. As described above, static data collection component 112 may include a means for collecting basic user data, such as basic anatomical data as well as subjective data (e.g. user preferences). For example, static data collection component 112 may comprise a user interface for entering manual measurements of user characteristics or attributes (e.g. a shoe size).

Static data collection component 112 may also comprise: image sensors, such as live or still cameras; scanners, such as optical and laser-based scanners; medical imaging systems, such as X-ray, Mill, or CAT scanners; and other sensor systems, such as pressure sensitive pads. For example, static data collection component 112 may comprise a camera used to photograph a user's body part, such as a user's foot. The digital photograph is thus 2D static user-specific data that may be used during the design of custom footwear.

Static data collection component 112 may also comprise a pressure sensitive pad that when stepped on by a user, generates 2D pressure data associated with the user's foot.

Dynamic data collection component 114 collects dynamic user-specific data. As described above, dynamic data collection component 114 may comprise pressure sensitive pads, wearable sensors, motion capture systems, or image capture systems. The aforementioned devices may generate 2D or 3D dynamic user-specific data.

For example, a user may walk or run down the length of a large pressure sensitive pad, which may record dynamic data as each foot lands, rotates, and then takes off again. Similarly, a user may jump up and down on a pressure sensitive pad. In some embodiments, live or still images may be collected concurrently with other sensor data (e.g. pressure pad data) so that the E2203.WO+ PATENT—17— sensor data can be juxtaposed with the actual physical movements of the user's foot for further analysis.

In some embodiments, a single sensor, such as a pressure sensitive pad, may be used to collect static user-specific data (e.g. when standing on a pad) and dynamic user-specific data (e.g. when walking, running, jumping, etc. on a pad). Similarly, an image sensor such as a camera may be used to collect static user-specific data (e.g. still images) as well as dynamic userspecific data (e.g. video or high-speed still images).

In some embodiments, data collection system 110 is portable and independent of other elements of custom footwear system 100, while in others it may be integral. Data collection system 110 may include sensors (e.g. pressure sensitive pads and cameras) as well as processing devices that support those sensors (e.g. mobile devices, computers, servers, and the like).

Data collection system 110 may comprise local data stores (not shown) and/or connections to remote data stores, such as data store 140. Data collected by data collection system 110 may be stored at local or remote data stores (or both) after being sensed, measured, determined, entered or otherwise created.

Data collection system 110 may be in data communication with other elements of custom footwear system 100 via, for example, hard-wired or wireless data connections. For example, in embodiments where data collection system 110 is portable and independent of other elements of custom footwear system 100, data collection system 110 may connect to those elements and share data via a network connection such as the Internet. In other embodiments, the connection may instead be ad-hoc between various elements.

Data processing system 120 is in data communication with data collection system 110. Data processing system 120 may receive static and/or dynamic data collected by data collection system 110 and use that data in the design of custom footwear.

For example, model design element 122 may take static user-specific data, such as image data, to build a 2D or 3D model of a user's body part, such as a foot. Model design element 122 may further take other static user-specific data, such as pressure sensitive data, and overlay it, or otherwise combine it with the 2D or 3D model. For example, a 3D model of a body part, such as a foot, could be further adapted using static pressure data such that the model shows the static pressure on different portions of the foot model. These differences could be depicted, for example, using color gradients, such as a "heat map." More particularly, the data could be rendered on the 2D or 3D model, or projected on a 2D projection of the 3D model, such as a 2D pressure distribution on the bottom of a user's foot.

Model design element 122 may further take dynamic user-specific data, such as pressure sensitive data, and overlay it, or otherwise combine it with a 2D or 3D model. For example, forces acting on a 3D model of a user's body part, such as a foot, could be depicted using the aforementioned heat map, or, for example, vectors that indicate the direction and magnitude of forces acting on the model of the user's foot. Myriad ways of combining the various types of user-specific data are known by persons of skill in the art.

Model design element 122 may further take statistical data, such as population data, and combine it with other user-specific data. For example, where only external characteristics of a user's body part are known (e.g. by image data), statistical data, such as a statistical shape model, may be used to supplement 2D or 3D models of a user's body part. For example, the predicted bone structure of a user's foot, given known external characteristics, could be built into a model using statistical shape models. Similarly, where only internal characteristics of a user's body part are known (e.g. by X-ray data), the predicted external structure of a user's foot could be built into a model using statistical shape models.

Model design element 122 may access statistical data from, for example, data store 140. Moreover, model design element 122 or footwear design element 124 may generate statistical data based on received user-specific data, and may store the generated statistical data locally or in data store 140.

Classifications regarding certain attributes of a user's body part (e.g. foot) may be made during the process of receiving user-specific data and designing a model of the user's body part. For example, static or dynamic pressure measurements of a user's foot on a pressure sensitive pad may be used to generate an "arch index." Further, the determined arch index may be used to classify the user's foot into one of a plurality of anatomical standard "arch types."

For example, measuring the contact surfaces of the forefoot, midfoot and heel, (hereinafter referred to as A, B, and C), may be used to determine an "arch index" (AI) according to the following equation: $B/(A+B+C)=AI$. Based on this equation, a user's arch type may be classified into categories, such as the following exemplary categories:

| | |
|---|---|
| Heavy High Arch Foot | 0% < AI < 7% |
| High Arch Foot | 7% < AI < 14% |
| Light High Arch Foot | 14% < AI < 21% |
| Normal Foot | 21% < AI < 28% |
| Light Flat Foot | 28% < AI < 35% |
| Flat Foot | 35% < AI < 42% |
| Heavy Flat Foot | 42% < AI < 100% |

Model design element 122 may include body part templates, such as 2D or 3D models meant be used as a starting point for a user-specific body-part model. In some cases, the templates may be based on statistical shape models, while in others the templates may be individually designed. Templates may be useful where user-specific data is sparse or inaccurate.

Footwear design element 124 may use received data, such as user-specific static and dynamic data, model data, classification data and the like to design a custom footwear model.

In some instances, footwear design element 124 may create a custom footwear portion, such as an insole, midsole, or outsole. Further, the design of the custom footwear portion may include one or more types of corrective features, such as microstructures, in order to influence the mechanical behavior of the footwear based on the footwear design model. In this way, custom footwear may be designed to correct or improve biomechanical function of, for example, a user's foot. Additionally, footwear design element 124 may determine an appropriate material or suggest a range of materials to be used when manufacturing the footwear.

For example, footwear design element 124 may be used to design a custom insole comprising microstructures that stiffen certain portions of the insole while promoting flexure in specified directions in other portions of the insole. And the custom insole may be manufactured from a particular material that is chosen for its physical characteristics (e.g. strength, elasticity, weight, etc.)

In some embodiments, footwear design element 124 may perform tests on a footwear design model to verify and validate the design. For example, footwear design element 124 may perform Fixed Element Analysis (FEA) or the like to verify the desired effects of various corrective features and to validate the model design as a whole. In this way, footwear design models can be thoroughly tested in a virtual environment before manufacturing the actual footwear.

Footwear design element 124 may include footwear templates, such as 2D or 3D models meant be used as a starting point footwear design models. In some cases, the templates may be based on statistical shape models, while in others the templates may be individually designed.

In some embodiments, footwear design element 124 includes programming configured to create footwear designs automatically based one or more models of a user's foot, such as those created by model design element 122. In such embodiments, footwear design element 124 may process a model of a user's body part, such as a foot, and determine one or more corrections that should be applied through a custom footwear design in order to, for example, treat a condition, prevent a condition, or improve performance. The programming used to automatically create footwear designs may rely on user-specific data as well as statistical data, such as population data, in order to determine an appropriate custom footwear design. In some embodiments, footwear design element 124 may allow an operator to select various footwear portions to be designed, such as bodies, insoles, midsoles, and outsoles, while in others, footwear design element 124 may decide automatically based on programming.

In some embodiments, footwear design element 124 is semi-automatic rather than fully automatic. In such embodiments, footwear design element 124 may, for example, automatically chose a template design and apply certain corrective features to it, but may stop at predetermined points during the design process to seek operator input regarding the design.

In other embodiments, footwear design element 124 may be used manually by a designer in order to create custom footwear designs. In such embodiments, a designer may be able to pick from a variety of options for the footwear design, such as what portions to design, and characteristics regarding those portions, including corrective features to be used in those portions. Further, a footwear portion, such as an insole, may be further divided into one or more zones for the purposes of the footwear design. And each zone may have individual characteristics designed to correct, improve, or otherwise alter the biomechanics of the foot.

Footwear design element 124 may be, for example, CAD or CAM software. In some embodiments, footwear design element 124 may be specialized CAD or CAM software that is configured to design custom footwear portions, such as bodies, insoles, midsoles, or outsoles. In some embodiments, model design element 122 and foot design element 124 are integral, such as when a single piece of software can perform both functions. In other cases, each element may be a separate module.

In some embodiments, data processing system 120 may include a model data processing element (not shown), which may be configured to perform a method of processing model data including: processing surface precursor data indicative of at least one characteristic for use in defining a surface of the object to be additively manufactured. In other embodiments, the method may additionally include: generating, based on the processed surface precursor data, surface data representative of a surface of at least part of the object to be additively manufactured; and generating slice data corresponding to at least one slice of the object to be additively manufactured. These and other embodiments are described in UK Patent Application No. GB1314421.7, entitled "Data Processing," which is incorporated herein by reference in its entirety.

Surface precursor data may be indicative of at least one characteristic for use in defining a surface of an object to be additively manufactured. Specifically, the surface being defined has a surface area and a configuration in 3D space. Thus, surface precursor data may be data that defines at least one precursor for use in defining the surface and may not directly represent a surface of an object. However, the surface precursor data may be used to calculate a part or of a whole surface of the object. As such, the surface precursor data may be considered to indirectly define a surface of at least part of an object to be additively manufactured. Notably, a line merely defining a contour of the surface may not define a surface of an object if the contour line does not define a surface having a surface area.

Using surface precursor may reduce the size of data files representative of an object to be additively manufactured compared with other data formats such as STL or AMF or others are as known in the art. Reducing the size of a data file representative of an object for additive manufacturing may result in increased transfer speed and efficiency over a data network (e.g. between data processing system 120 and manufacturing system 130). Further, hardware requirements of a computer and network requirements such as available bandwidth may be advantageously reduced as a result of the reduced data file size. Finally, reducing the size of the data file may increase the speed and efficiency of processing the data file (compared with known data formats such as STL and AMF formats) to generate, for example, slice data for instructing an additive manufacturing device, such as additive manufacturing device 134.

In particular, using surface precursor data may also reduce the size of data files representative of an object to be additively manufactured where the object includes complex structures, such as porous structures, mesh structures, lattice structures, and structures with intricate surface detail. In known data formats such as STL and AMF, the configuration of a surface of an object to be additively manufactured is directly represented by data representative of a triangular mesh, i.e. a plurality of tessellating triangles. Note that a surface of an object is a surface area defining an extent of any part of the object. The surface can therefore define external surfaces of an object, and internal surfaces of an object, for example, which define a cavity or a porous structure within the object. For defining more complex surfaces, such as the surface of a porous structure, smaller triangles are used in known methods to provide the increased granularity needed to describe the complex surface. Using smaller triangles to defined more complex surfaces results in a greater number of triangles needed to define any surface of the object. In known data formats such as STL and AMF, each triangle of the triangular mesh is encoded by coordinate data for each of the three vertices of the triangle. Therefore, when determining a large number of small triangles to describe a complex surface, the size of the resulting data file can become too large to be practically transmitted and/or processed.

In some embodiments, data processing system 120 is portable and independent of other elements of custom footwear system 100, while in others it may be integral. For example, data processing system 120 could be a computer system, such as a laptop computer, which is portable. In other embodiments, data processing system 120 may be remote from other elements of custom footwear system 100. For example, data processing system 120 may be a remote server that receives data over data links and processes that data remotely.

Data processing system 120 may comprise local data stores (not shown) and/or connections to remote data stores, such as data store 140. The output of model design element 122 (e.g. a user-specific body part model) and footwear design element (e.g. a custom footwear model) may be stored in data store 140.

Data processing system 120 may be in data communication with other elements of custom footwear system 100 via, for example, hard-wired or wireless data connections. For example, in embodiments where data processing system 120 is portable and independent of other elements of custom footwear system 100, data processing system 120 may connect to those elements and share data via a network connection such as the Internet. In other embodiments, the connection may instead be ad-hoc between various elements.

Manufacturing system 130 may comprise a controller 132 and an additive manufacturing device 134. Manufacturing system 130 may receive data from data processing system 120 in order to manufacture custom footwear or custom footwear portions, such as insoles, midsoles, and outsoles. For example, manufacturing system 130 may receive custom footwear design data in the form of "STL" or "PLY"

formatted files from data processing system 120, which may be interpreted by controller 132 in order to drive additive manufacturing device 134. Manufacturing system 130 will be described in more detail, below, with respect to FIG. 7.

Notably, the lines of data communication depicted between data collection system 110, data processing system 120, manufacturing system 130, and data store 140 in FIG. 1 are representative only. The data communication paths between the various elements of custom footwear system 100 may be direct or indirect, may traverse a single or multiple networks, may include intervening devices, may be wired or wireless, may use different protocols, may use different mediums, etc. Moreover, the data communication paths may be one-way or two-way such that data may be shared between various elements.

In some embodiments, the elements of custom footwear system 100 depicted in FIG. 1 may be integrated into a single system. In such embodiments, a user may be able to be scanned (e.g. using image sensors) and tested (e.g. using pressure sensitive pads) and subsequently receive custom footwear or custom footwear portions, such as a body, an insole, a midsole, or an outsole, all in the same place. In such embodiments, an operator may be present to take part in or at least validate the design of the custom footwear. However, in other embodiments, the entire process may be automated. For example, in some embodiments, the entire custom footwear system 100 may be a kiosk or the like at a footwear store, sporting goods store, or the like.

In other embodiments, the elements of custom footwear system 100 may be separate. For example, the data collection system 110 may be separate from the data processing system 120 and the manufacturing system 130 (though the latter two systems may be integral or co-located). For example, a kiosk or the like may include a data collection system comprising various sensors, such as image sensors and pressure sensitive pads, which are in data communication with a data processing system 120 and manufacturing system 130 in another location. Notably, while these various elements may be physically separate in certain embodiments, they may still be co-located at a particular location, such as a footwear store in order that a user could be scanned and provided with custom footwear at the same location.

In yet other embodiments, the data collection system 110 and the manufacturing system 130 may be co-located, while the data processing system 120 is in a separate location. Due to the complex processing performed by the data processing system 120, it may be desirable to locate the data processing system 120 apart from the data collection system 110 and the manufacturing system, such as in a remote server location. For example, a footwear store may have the data collection system 110 and manufacturing system 130 in the same location, while the data processing system (and potentially its operator) are located in a completely different location. In this way, sellers of custom footwear could limit the cost and space associated with every element and only have those elements of the custom footwear system 100 that are most convenient to users. Such embodiments would also allow purveyors of custom footwear systems to utilize different equipment distribution and sales models. For example, a custom footwear system purveyor could sell certain elements of the system, such as the data collection system, while offering a subscription model to other elements, such as the data processing system. Ultimately, the custom footwear system 100 may be as integral or modular as is necessary for a particular end-user of the system.

Figure 2:
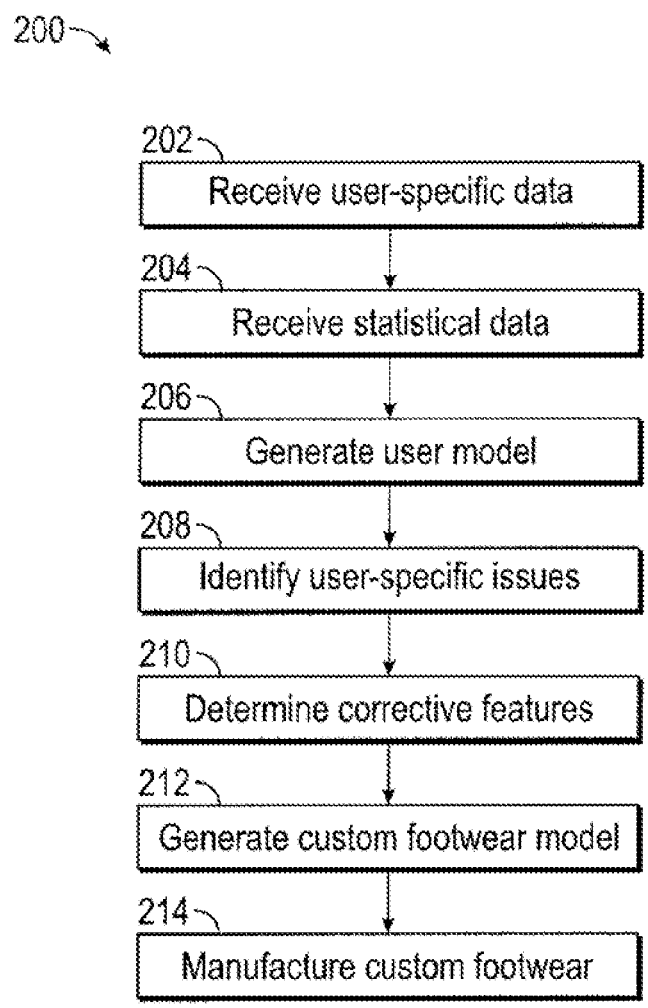
FIG. 2 depicts a method for designing custom footwear.

FIG. 2 depicts a method 200 for designing custom footwear, such as a body, an insole, a midsole, or an outsole.

The method 200 begins at step 202, where user-specific data is received. As described above, user-specific data may include static or dynamic user-specific data. And the user-specific data can be received from, for example, a data collection system, such as data collection system 110 described with reference to FIG. 1.

The method 200 then moves to step 204, where statistical data is received. As described above, statistical data may include, for example, statistical shape models of different anatomical features based on population data. However, other statistical data is also possible. For example, basic measurements based on a known user's shoe size can be used.

The method 200 then moves to step 206, where a user model is generated. As described above, the user model may be a 2D or 3D model of a user's body part, such as a user's foot. The user model may be based on some or all of the user-specific data received at step 202 and the statistical data received at step 204. In some embodiments, such as where little if any reliable user-specific data is received, the user model may be generated based primarily on statistical data or on a template, or on both.

The user model may generated in step 206 may include many additional features beyond mere 2D or 3D shape data. For example, the user model may be supplemented with static or dynamic data, such as pressure data. This data may be enhance the model so that appropriate custom footwear can be designed for the user.

The method 200 then moves to step 208, where user-specific issues or problems are identified based on the user model.

In some embodiments, user-specific issues are determined based on comparing the user model to, for example, an ideal model of a body part, such as a foot. The user model may be compared to shape models as well as performance models (e.g. ideal pressure distribution models). In some embodiments, the user model includes dynamic data that is compared with "ideal" dynamic data (e.g. footfall models). In other embodiments, the use model may be compared to templates or statistical shape models to identify potential issues. Issues such as pronation, supination, bunion, misalignment, flat foot, arch issues, performance issues and others may be identified based on the user model.

In other embodiments, user-specific issues may be identified based on a manual review of the user model by, for example, a trained technician, or by an orthopedic doctor, or the like. In such a scenario, the issues may be identified manually, but the resulting corrective features may be generated automatically.

The method 200 then moves to step 210, where corrective features are determined in order to address one or more of the user-specific issues identified in step 208. As described above, many types of corrective structures, including microstructures, may be used to design corrective footwear.

For example, appropriate microstructures may be determined to prevent unwanted movement in selected directions while allowing free movement in other directions. Similarly, thickness adjustments to various zones in a footwear portion may be determined in order to provide more uniform support. Other corrective features, as described above, may also be determined.

The method 200 then moves to step 212, where a custom footwear model is generated. For example, the custom footwear model may comprise a footwear portion, such as a body, an insole, a midsole, or an outsole.

In some embodiments, the custom footwear model is initially a footwear template, which may be only partially customized based on basic user-specific data. For example, the custom footwear model may start as a body, an insole, a midsole, or an outsole template for a user with a certain shoe size. The template may then be further customized to, for example, incorporate one or more of the corrective structures determined in step 210.

In some embodiments, an initial template may be based on certain classifications or categorizations of anatomical types, such as the various types of foot arches described above. Such classification or categorizations related to a user's body part may increase the speed and accuracy of an initial model based on a template.

In other embodiments, the custom footwear model is not generated from a template, but rather is generated almost entirely based on user-specific data. This may be the case where comprehensive user-specific data exists for a particular user.

In some embodiments, the custom footwear model is generated automatically by appropriate software. In other embodiments, the custom footwear model may be generated semiautomatically, or completely manually.

The method 200 then moves to the final step 214, where the custom footwear, such as a body, an insole, a midsole, or an outsole, is manufactured.

In some embodiments, the custom footwear is manufactured using additive manufacturing techniques, such as those described above, and others as are known in the art. As described above, the manufactured custom footwear may address user-specific problems, as well as help to prevent injuries and the onset of foot conditions, or even improve biomechanical performance (e.g. for athletes).

Figure 3A:
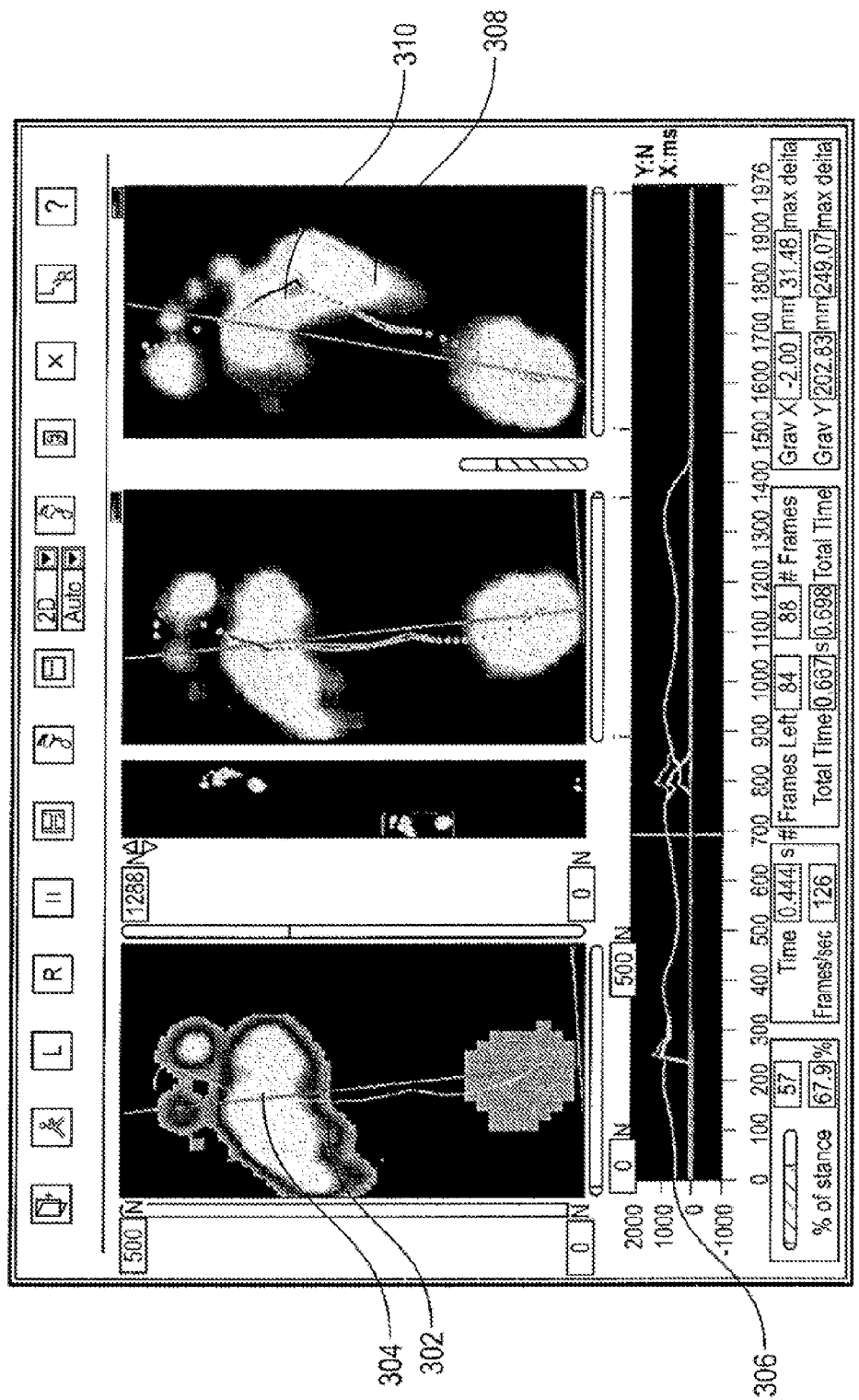
FIG. 3A depicts a graphical user interface of an exemplary data collection system.

FIG. 3A depicts a graphical user interface of an exemplary data collection system, such as data collection system 110 in FIG. 1. In FIG. 1, dynamic user-specific foot pressure data 302 is displayed on a graphical user interface. In this embodiment, the pressure data 302 indicates the pressure applied to a pressure sensitive pad at a particular point in time. In this embodiment, the pressure data is color coded such that certain colors indicate higher pressures than other colors.

FIG. 3A also depicts a determined vector 304 indicating the midpoint and direction of the average pressure applied by a user's foot to the pressure sensitive pad at a particular point in time.

FIG. 3A also depicts dynamic pressure data 306 indexed against time. This data may be useful for identifying where in a user's dynamic movement pressure is maximized so that corrective structures can be designed to reduce the maximum pressure points. The determined vector may be useful to determine alignment of a user's stride and footfall, or to determine balance characteristics of a user's step.

FIG. 3A also depicts average dynamic data 308. The average dynamic data shows the average pressure of the user's foot on the pressure sensitive pad over many steps. In particular, a "hot spot" 310 (i.e. area of relatively higher pressure) is determined by viewing the average dynamic data 308. Hot spot 310 may be identified as a user-specific problem, such as described with respect to step 208 in FIG. 2.

The user-specific data depicted in FIG. 3A may be sent to, for example, a data processing system such as data processing system 120 depicted in FIG. 1, and used by that system to generate or supplement a user model.

Figure 3B:
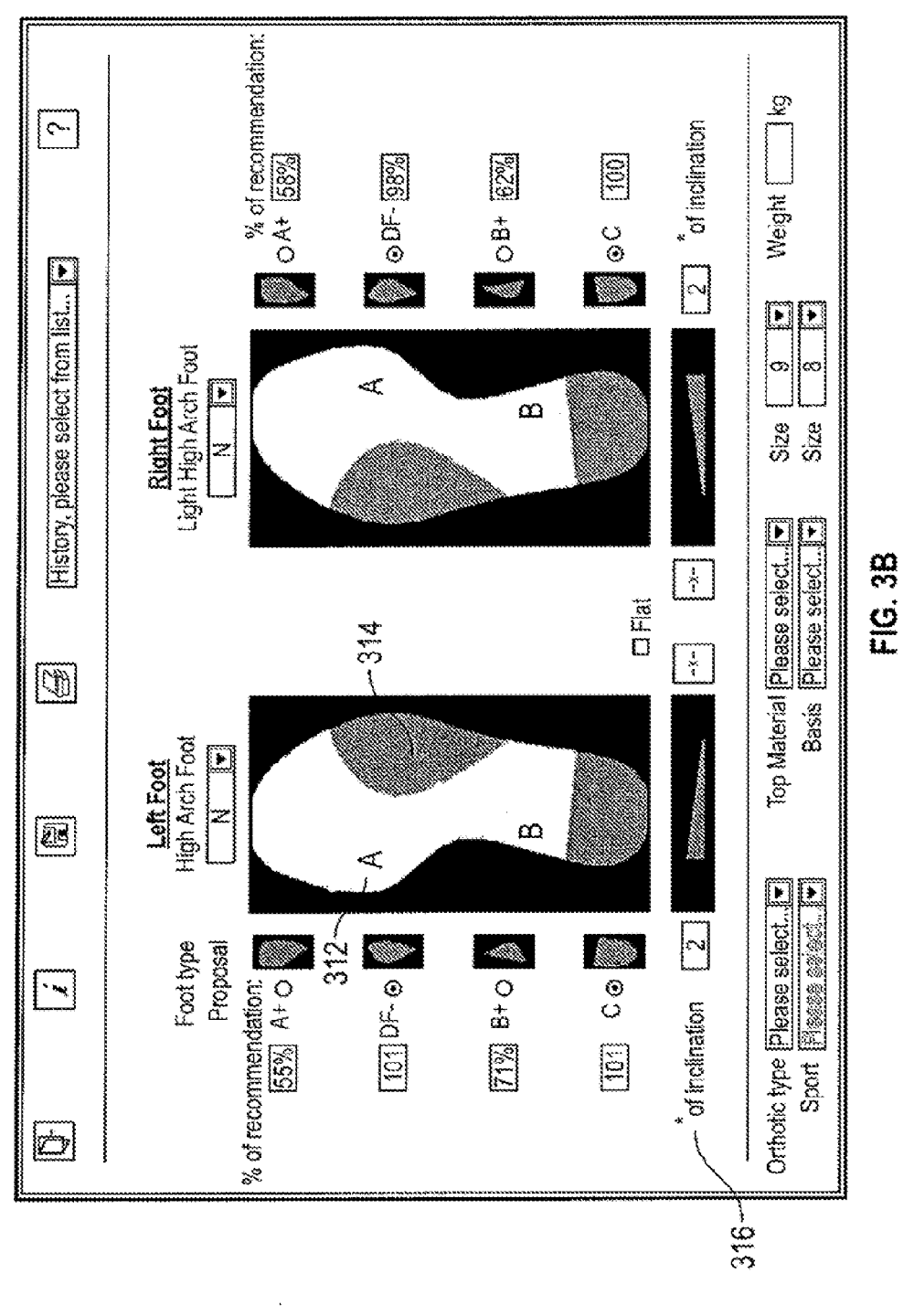

FIG. 3B depicts a graphical user interface of an exemplary footwear design component, such as footwear design component 124 of data processing system 120 depicted in FIG. 1. Specifically, FIG. 3B depicts an exemplary footwear portion 312 (here an insole) including a plurality of zones (e.g. zone 314). The footwear portion 312 includes corrective structures, such as thickened portions (as indicated by inclination angle 316).

Notably, FIG. 3B is only a single embodiment of a footwear design component. Different embodiments with more comprehensive design capabilities are envisioned.

Figure 4A:
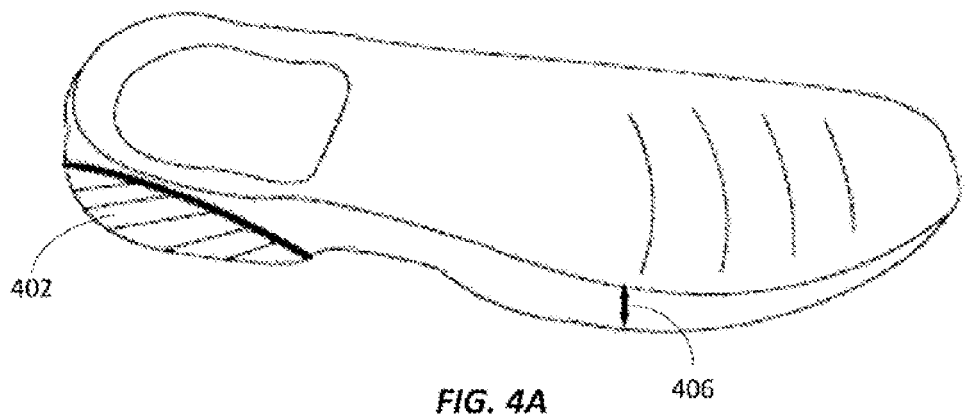
FIGS. 4A-4C depict exemplary midsoles (footwear portions), which include corrective features.
Figure 4B:
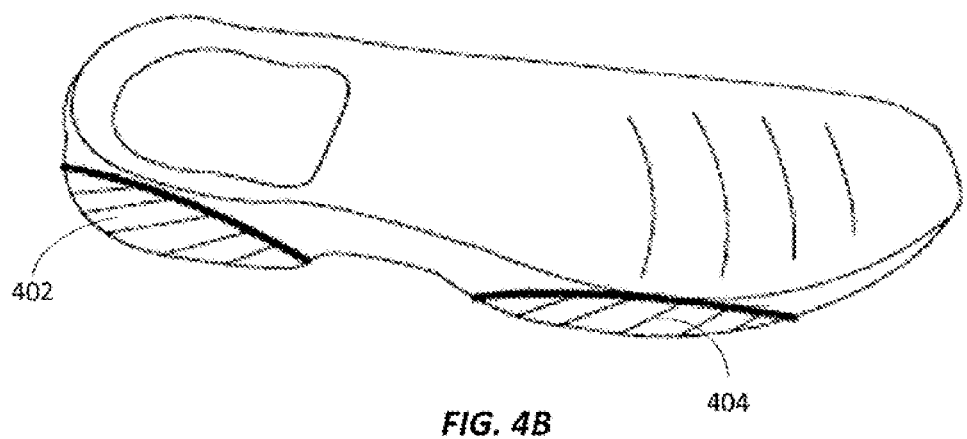
Figure 4C:
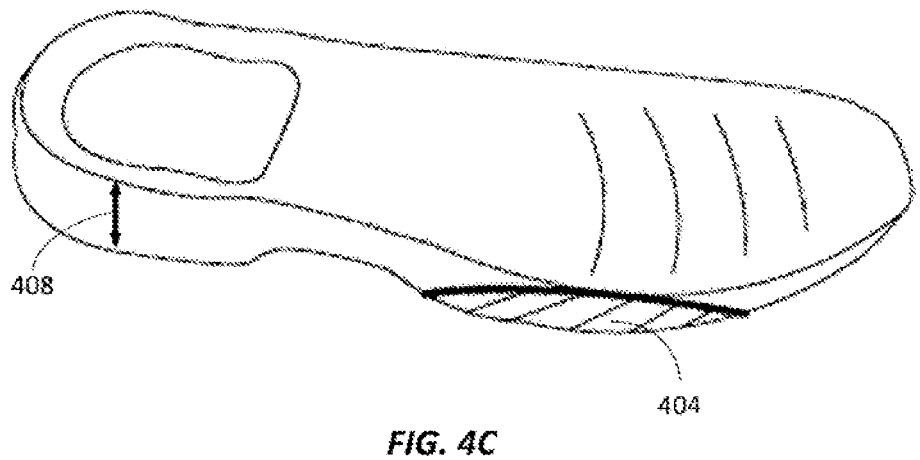

FIGS. 4A-4C depict exemplary midsoles designed based on dynamic user-specific data, which include corrective features meant to improve comfort and reduce injury. Specifically, FIG. 4A depicts a midsole (footwear portion) for a user that tends to land on the heel portion of the user's foot when walking and running. Accordingly, the midsole of FIG. 4A comprises a viscoelastic member 402 (corrective feature) in the heel portion for optimal shock absorption.

FIG. 4B depicts a midsole (footwear portion) for a user that tends to land on the center portion of the user's foot when walking and running. Accordingly, the midsole of FIG. 4B comprises visco-elastic members 402 and 404 (corrective features) in the heel and fore-foot portions in order to distribute the shock of footfalls.

FIG. 4C depicts a midsole (footwear portion) for a user that tends to land on the fore-foot (or toe) portion of the user's foot when walking and running. Accordingly, the midsole of FIG. 4C comprises a visco-elastic member 404 (corrective feature) in the forefoot portion for optimal shock absorption.

Regarding FIGS. 4A-4C, the base thickness 406 of the midsoles may be determined, for example, based on: the intended use of the footwear (in particular, the running speed); the weight of the user; the load of the fore-foot; the need for local corrections; and the landing pattern of the user. Further, the thickness of the midsole may be varied from the heel to the mid-foot, to the fore-foot portions.

Additionally, the height of the heel 408 and the corresponding heel drop (i.e. the difference between the height of the heel portion and the fore-foot portion) of the midsoles depicted in FIGS. 4A-C may be determined based on the aforementioned parameters, as well as other parameters, such as the degree of pronation or supination in the user's stance. Similarly, the bead drop (i.e. the difference between the height of the mid-foot portion and the forefoot portion) of the midsoles may be determined based on the user's landing pattern or the user's desired running speed, or other characteristics as are known in the art.

For example, a user that lands predominately on the heel may benefit from a lower heel drop as compared to a user that lands predominately on the mid-foot. And a user that lands predominately on the mid-foot may require a lower heel drop than a user that lands primarily on the fore-foot. As another example, the bead drop may be increased based on the user's target walking or running speed.

Finally, the height of the "rocker" (i.e. the recess below the front part of the sole, which ensures that the sole is in contact with the ground during the roll) of the midsoles depicted in FIGS. 4A-C may be determined based on user characteristics and preferences, such as whether the user is primarily a runner or walker.

Figure 5A:
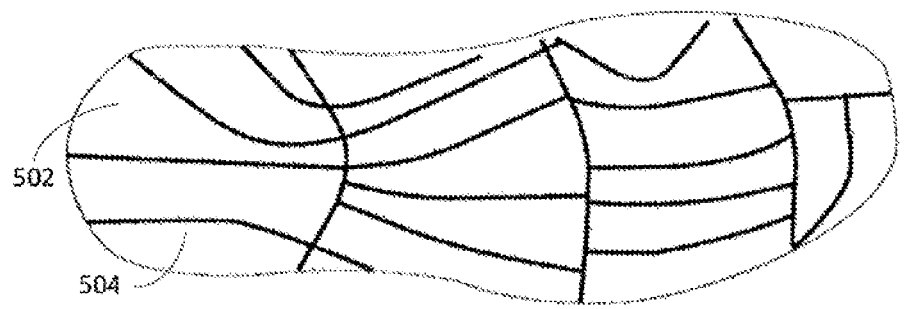
FIGS. 5A-5B depict exemplary insoles (footwear portions) comprising a plurality of corrective zones.
Figure 5B:
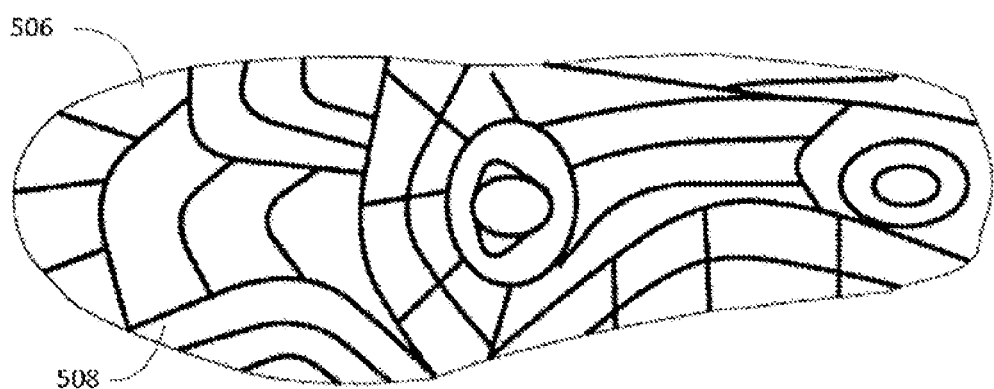

FIGS. 5A and 5B depict insoles (footwear portions) comprising a plurality of areas or "zones" (e.g. 502, 504, 506, and 506). In the depicted embodiments, each zone comprises different microstructures in order to vary the mechanical properties of the footwear portion in each zone. For example, the microstructures may contribute to the hardness, compressibility, elasticity, bendability, etc. of each particular zone. In some embodiments, a zone may comprise many microstructures of like or dissimilar types. In other embodiments, a zone may comprise a single microstructure.

In FIGS. 5A and 5B, the various zones were determined based on user-specific data (e.g. anatomical properties and dynamic measurements of the foot). In particular, the embodiments in FIGS. 5A and 5B were designed (e.g. using a footwear design element such as that depicted in FIG. 1) in order to minimize the impact of the foot on the skeleton, joints, muscles, tendons, and the like. Further, the various zones influence the mechanical characteristics of the footwear in use. For example, the zones in the fore-foot region may be relatively more flexible to allow for rolling of the foot, while the zones in the heel portion of the sole especially may prevent rotation, particularly side-to-side rotation to avoid ankle injury.

The microstructures and other features of the custom footwear portions depicted n FIGS. 5A and 5B may be built up in several layers, wherein each layer comprises the same or different microstructures. By designing the footwear portions in non-homogeneous layers, more complex mechanical characteristics (e.g. compression, flexure, etc.) can be obtained compared to footwear portions made of a single, uniformly distributed material.

Figure 6A:
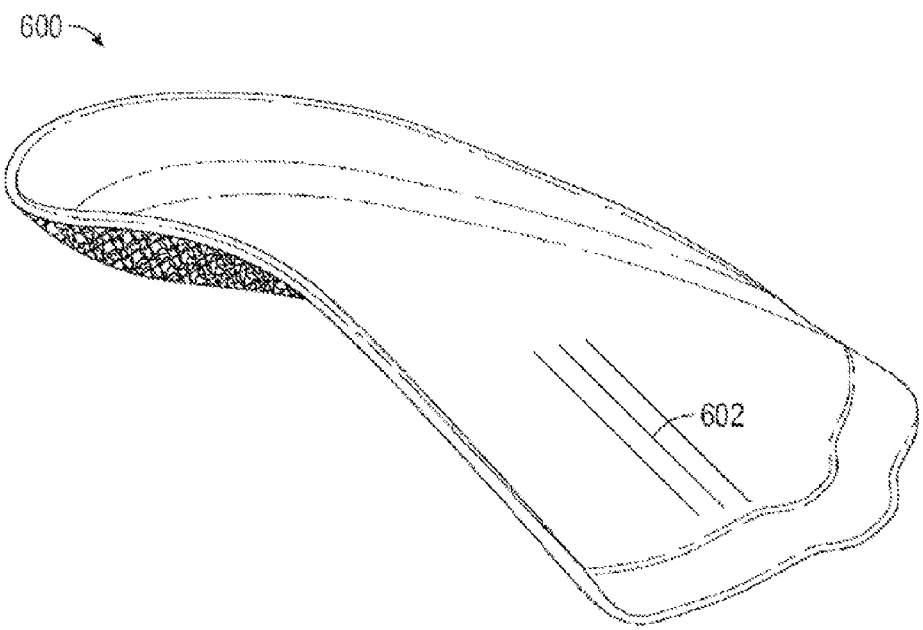
FIGS. 6A-6B depict an additively manufactured insole (footwear portion).
Figure 6B:
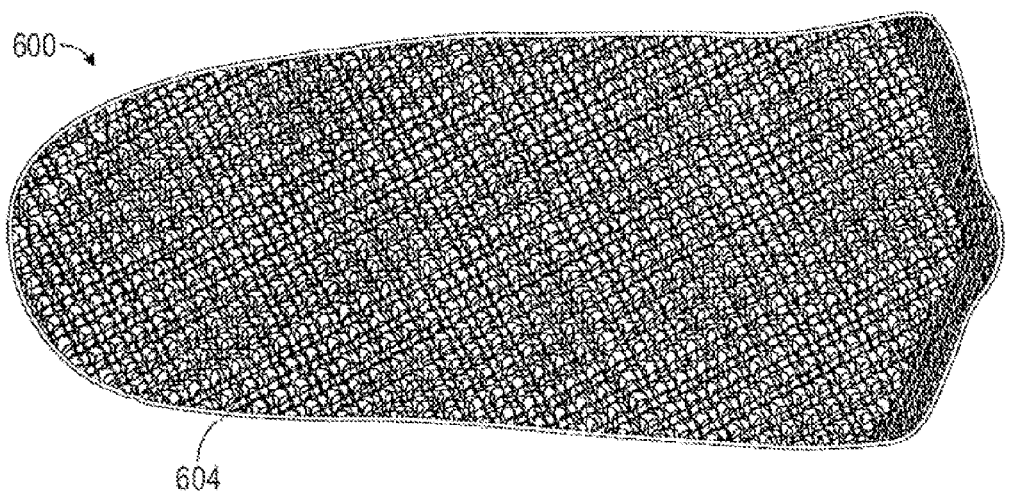

FIGS. 6A and 6B depict an additively manufactured custom footwear portion 600 from different angles (roughly top and bottom). Custom footwear portion 600 is based on userspecific data, such as that described above and with respect to data collection system 110 of FIG. 1. The design of custom footwear portion 600 was created with a data processing system like that described and depicted with reference to FIG. 1. Finally, custom footwear portion 600 was additively manufactured using techniques such as those described above with an additive manufacturing system like that described and depicted with reference to FIGS. 1 and 7.

Custom footwear portion 600 includes corrective features. For example, the overall thickness of custom footwear portion 600 has been varied purposefully to affect a user's weight distribution and to promote proper foot movement and comfort. Custom footwear portion 600 also comprises ribs 602 (as depicted in FIG. 6A), which promote bending in a designed direction and counteract bending in other directions. Finally, custom footwear portion also comprises corrective microstructures 604 (as depicted in FIG. 6B).

As is depicted in FIG. 6B, the microstructures 604 are complex 3D cellular structures that have been created layer-by-layer using, for example, an additive manufacturing technique such as described above. The axes of the microstructures in the embodiment depicted in FIG. 6*b* are orientated to affect the torsional resistance of custom footwear portion 600.

In some embodiments, the axes of the microstructures are not necessarily parallel in each area or zone of the custom footwear portion. For example, in some embodiments, the axes of the microstructures fan out from a common point, such as a point in the heel area.

Figure 7:
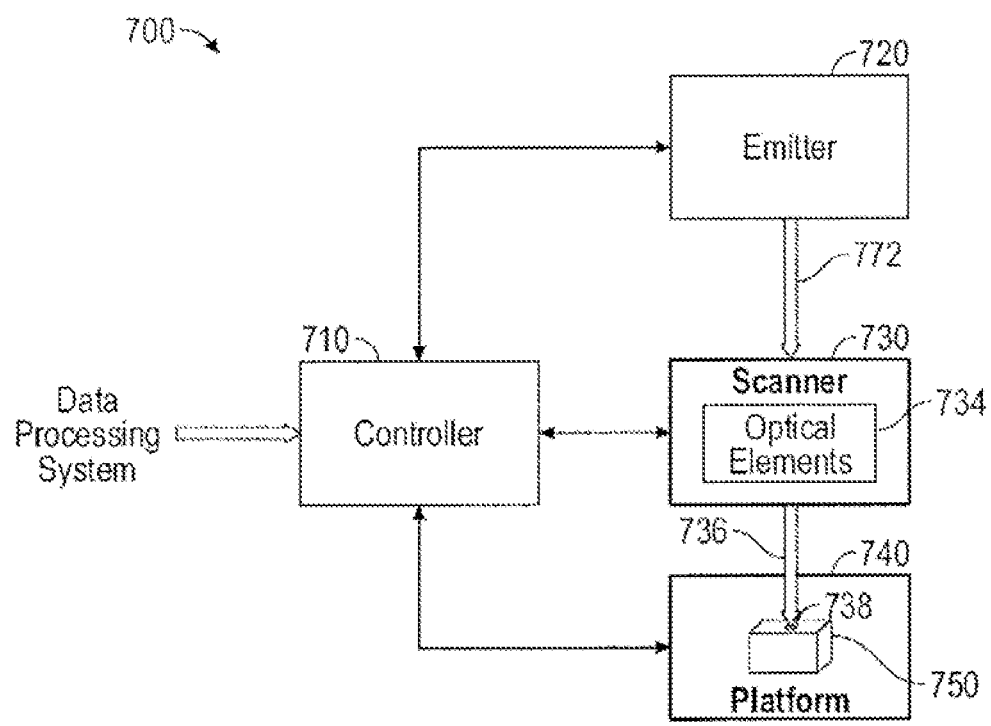
FIG. 7 depicts an exemplary additive manufacturing apparatus.

FIG. 7 depicts an exemplary additive manufacturing apparatus 700 that may be configured to perform additive manufacturing techniques such as SLA, SLS, and SLM, and others as are known in the art, in order to manufacture custom footwear, such as the custom footwear portions depicted in FIGS. 6A and 6B.

Additive manufacturing apparatus 700 includes a controller 710, which is in data communication with an emitter 720, a scanner 730, and a platform 740. Notably, a similar additive manufacturing apparatus for performing FDM may substitute the emitter 720 and scanner 730 for an extrusion nozzle and associated mechanical controls.

Controller 710 may be, for example, a computer system with software for operating additive manufacturing apparatus 700. In other embodiments, controller 710 may be embodied as a general purpose processor, a digital signal processor (DSP), an application-specific integrated circuit (ASIC), a field-programmable gate array (FPGA) or other programmable logic device, discrete gate or transistor logic, discrete hardware components, or any suitable combination thereof designed to perform the functions described herein as are known by those of skill in the art.

As with before, the lines of data communication depicted between controller 710 and emitter 720, scanner 730, and platform 740 in FIG. 7 are representative only.

Controller 710 may control emitter 720. For example, controller 710 may send data signals to emitter 720 in order to power on and off the emitter. Additionally, controller 710 may control the output power of emitter 720. In some embodiments, controller 710 may control multiple emitters 720 (not shown) in the same additive manufacturing apparatus 700. In some embodiments, emitter 720 may additionally send data back to controller 710. For example, emitter 720 may send operational parameters such as power output, power use, temperature, and other operational parameters as are known in the art. The operational parameters of emitter 720 may be used by controller 710 to further control or optimize the processing of object 750.

Controller 710 may also control scanner 730. For example, controller 710 may cause the selection, manipulation, articulation, engagement or other use of optical elements 734. For example, controller 710 may cause a focusing lens element to move in order to affect the size of a resulting beam 736 or a size of a resulting beam spot 738. Further, controller 710 may cause a mirror or similar optical element to redirect resulting beam 736 in different directions and onto different locations of object 750. As yet another example, controller 710 may cause a shutter or similar optical element to mask resulting beam 736 even while emitter 720 is active.

In some embodiments, controller 710 may receive data back from scanner 730. For example, scanner 730 may send operational parameters such as power output, power use, temperature, beam size selection, beam power, beam direction, beam spot position, position of optical elements, condition of optical elements, and other operational parameters as are known in the art. The operational parameters of emitter 720 may be used by controller 710 to further control or optimize the processing of object 750. In some embodiments, controller 710 may be a part of scanner 730.

Controller 710 may also control platform 740. For example, controller 710 may cause platform 740 to move in one or more dimensions (e.g. up and down or side to side). Controller 710 may receive operational data from platform 740, such as position, temperature, weight, proximity, and others as are known to persons of skill in the art. Controller 710 may cause platform 740 to move in increments of one layer of object 750 at a time so that scanner 730 can process a layer of material to add to object 750. Layers of object 750 may be defined in three dimensional design drawings (e.g. 3D CAD) or in one or more two dimensional cross-sectional drawings (e.g. 2D CAD).

In some embodiments, controller 710 may store or otherwise have access to object design data, such as 3D CAD drawings of an object to be manufactured by optical additive manufacturing apparatus 700. For example, controller 710 may be a part of a computer system that also includes object design software and hardware, such as CAD software. In this way, controller 710 may have access to object design data in order to control emitter 720, scanner 730, and platform 740 and to manufacture object 750. In other embodiments, controller 710 may be connected by a communication path to a repository, database, or the like of design data, such as database 760 in FIG. 7.

In some embodiments, controller 710 may receive footwear design data from, for example, data processing system 120 of FIG. 1. In this way, controller 710 may direct the additive manufacturing of custom footwear, including custom footwear portions such as insoles, midsoles, and outsoles.

Emitter 720 may be, for example, a laser emitter, such as a diode laser, pulsed laser, or fiber layer, or other types of laser as are known by those of skill in the art. In some embodiments, the emitter 720 may be an ultraviolet laser, carbon dioxide laser, or ytterbium laser. Emitter 720 may be other types of irradiating emitters as known by those of skill in the art.

Emitter 720 emits a beam, for example laser beam 722, which is then processed by scanner 730. Notably, while not shown in FIG. 7, optical elements such as mirrors, lenses, prisms, filters, etc., may be located between the emitter 720 and scanner 730.

In some embodiments, emitter 720 may be a part of scanner 730. [0189] Scanner 730 may include optical elements 734. For example, optical elements may include lenses, mirrors, filters, splitters, prisms, diffusers, windows, displacers, and other elements as are known in the art. The optical elements 734 may be fixed or moveable based on data received by scanner 730 or controller 710.

Scanner 730 may also include sensors (not shown) that sense various operating parameters during operation of the scanner 730. Generally speaking, the sensors may provide data feedback to the scanner 730 and or controller 710 in order to improve calibration and manufacturing performance of optical additive manufacturing apparatus 700.

For example, scanner 730 may include position sensors, heat sensors, proximity sensors, and the like. Additionally, scanner 730 may include one or more image sensors. The image sensors could be used to provide visual feedback to an operator of optical additive manufacturing apparatus 700. The image sensors could also be used, for example, to analyze the size, focus and position of the beam spot incident on the object being manufactured for calibration and precise tracking. Further, the image sensor may be sensitive to heat (e.g. a thermal image sensor) and be used to determine the state of the underlying material (e.g. resin) as it is being processed. For example, a thermal image sensor may measure the local heating around the beam spot and/or the level of curing of the material being processed.

Platform 740 acts as a moveable base for the manufacture of object 750, which may be custom footwear. As described above, platform 740 may move in one or more directions and be controlled by a controller, such as controller 710. For example, platform 740 may be controlled by controller 710 and moved one layer or cross-section of object 750 at a time during the manufacture of object 750.

Platform 740 may include sensors that determine operational data and transmit that data to controller 710 or to other parts of optical additive manufacturing apparatus 700.

Platform 740 may be enclosed by a container or vessel (not shown) containing manufacturing materials (e.g. photosensitive resin) that is processed by an incident beam spot directed by scanner 730. For example, scanner 730 may direct a beam over a layer of photosensitive resin, which causes the resin to cure and form a permanent layer of object 750.

Platform 740 may be made of any suitable material of adequate strength and resilience to serve as a manufacturing base for objects like object 750.

In addition to a container or vessel around platform 740, additive manufacturing apparatus 700 may also include a manufacturing material dispensing element. For example, an element may dispense a new layer of manufacturing material after each respective layer of object 750 is completed by the action of scanner 730.

Object 750 is formed by additive manufacturing apparatus 700 using various methods, such as SLA, SLS, SLM and others as are known by those of skill in the art.

Figure 8:
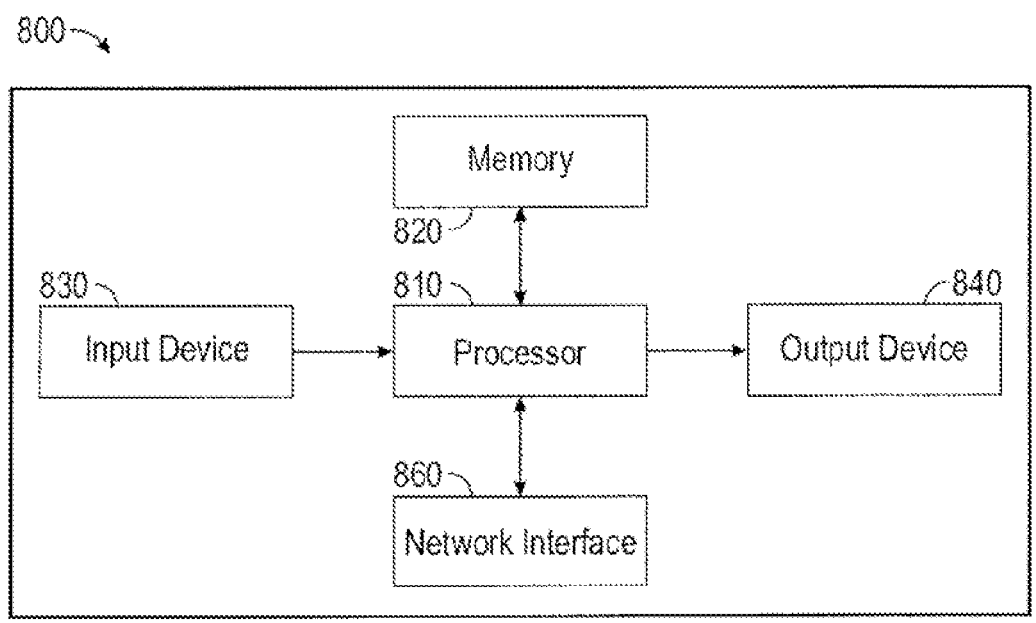
FIG. 8 depicts an exemplary computing device.

FIG. 8 depicts an exemplary computing device 800, such as may be used in connection with data collection system 110, data processing system 120, and/or manufacturing system 130 of FIG. 1.

The computing device 800 includes a processor 810. The processor 810 is in data communication with various computer components. These components may include a memory 820, an input device 830, and an output device 840. In certain embodiments, the processor may also communicate with a network interface card 860. Although described separately, it is to be appreciated that functional blocks described with respect to the computing device 800 need not be separate structural elements. For example, the processor 810 and network interface card 860 may be embodied in a single chip or board.

The processor 810 may be a general purpose processor, a digital signal processor (DSP), an application specific integrated circuit (ASIC), a field programmable gate array (FPGA) or other programmable logic device, a discrete gate or transistor logic, discrete hardware components, or any suitable combination thereof designed to perform the functions described herein. A processor may also be implemented as a combination of computing devices, e.g., a combination of a DSP and a microprocessor, a plurality of microprocessors, one or more microprocessors in conjunction with a DSP core, or any other such configuration.

The processor 810 may be coupled, via one or more data buses, to read information from or write information to memory 820. The processor may additionally, or in the alternative, contain memory, such as processor registers. The memory 820 may include processor cache, including a multi-level hierarchical cache in which different levels have different capacities and access speeds. The memory 820 may further include random access memory (RAM), other volatile storage devices, or non-volatile storage devices. The storage can include hard drives, optical discs, such as compact discs (CDs) or digital video discs (DVDs), flash memory, floppy discs, magnetic tape, Zip drives, USB drives, and others as are known in the art.

The processor 810 may also be coupled to an input device 830 and an output device 840 for, respectively, receiving input from and providing output to a user of the computing device 800. Suitable input devices include, but are not limited to, a keyboard, a rollerball, buttons, keys, switches, a pointing device, a mouse, a joystick, a remote control, an infrared detector, a voice recognition system, a bar code reader, a scanner, a video camera (possibly coupled with video processing software to, e.g., detect hand gestures or facial gestures), a motion detector, a microphone (possibly coupled to audio processing software to, e.g., detect voice commands), or other device capable of transmitting information from a user to a computing device. The input device may also take the form of a touch-screen associated with the display, in which case a user responds to prompts on the display by touching the screen. The user may enter textual information through the input device such as the keyboard or the touch-screen. Suitable output devices include, but are not limited to, visual output devices, including displays and printers, audio output devices, including speakers, headphones, earphones, and alarms, additive manufacturing devices, and haptic output devices.

The processor 810 further may be coupled to a network interface card 860. The network interface card 860 prepares data generated by the processor 810 for transmission via a network according to one or more data transmission protocols. The network interface card 860 may also be configured to decode data received via the network. In some embodiments, the network interface card 860 may include a transmitter, receiver, or both. Depending on the specific embodiment, the transmitter and receiver can be a single integrated component, or they may be two separate components. The network interface card 860, may be embodied as a general purpose processor, a DSP, an ASIC, a FPGA, or other programmable logic device, discrete gate or transistor logic, discrete hardware components, or any suitable combination thereof designed to perform the functions described herein.

The invention disclosed herein may be implemented as a method, apparatus, or article of manufacture using standard programming or engineering techniques to produce software, firmware, hardware, or any combination thereof. The term "article of manufacture" as used herein refers to code or logic implemented in hardware or non-transitory computer readable media such as optical storage devices, and volatile or non-volatile memory devices or transitory computer readable media such as signals, carrier waves, etc. Such hardware may include, but is not limited to, FPGAs, ASICs, complex programmable logic devices (CPLDs), programmable logic arrays (PLAs), microprocessors, or other similar processing devices.

It will be appreciated by persons skilled in the art that numerous variations and/or modifications may be made to the invention without departing from the spirit or the scope of the invention as broadly described. The above described embodiments are, therefore, to be considered in all respects as illustrative and not restrictive.

What is claimed is:

1. A method of designing a custom footwear model based on a user model, the method comprising:
    receiving user data associated with a user, wherein the user data comprises dynamic data measurements of user movements;
    generating the user model based on the received user data and statistical foot data associating at least one type of foot characteristic provided in the user data with a different type of foot characteristic not provided in the user data, the user model comprising a model of a foot of the user;
    determining one or more issues specific to the user based on a comparison of the user model to one or more foot statistical shape models;
    determining one or more corrective features for addressing the one or more issues based on the comparison of the user model to the one or more foot statistical shape models, wherein the one or more corrective features comprise a microstructure having a size and position configured to address the one more issues; and
    generating the custom footwear model comprising the one or more determined corrective features, wherein a footwear part is created layer by layer based on the custom footwear model using additive manufacturing.

2. The method of claim 1, wherein the user data includes one or more of: foot pressure data, gait data, body data, or image data.

3. The method of claim 1, wherein the footwear part is one of an insole, a midsole, or an outsole.

4. The method of claim 2, wherein the footwear part comprises the microstructure.

5. The method of claim 1, wherein the footwear part is configured to alter a biomechanical action of the user's foot.

6. The method of claim 1, wherein the footwear part is configured to improve a static weight distribution of a user's foot.

7. An apparatus configured to design a footwear part, comprising:
    a data store comprising footwear template models and executable software;
    a sensor configured to create user data; and
    a processor in data communication with the data store and the sensor, wherein the processor is configured to execute the software and cause the apparatus to:
        receive the user data associated with a user, wherein the user data comprises dynamic data measurements of user movements;
        generate a user model based on the received user data and statistical foot data associating at least one type of foot characteristic provided in the user data with a different type of foot characteristic not provided in the user data, the user model comprising a model of a foot of the user;
        determine one or more issues specific to the user based on a comparison of the user model to one or more foot statistical shape models;
        determine one or more corrective features for addressing the one or more issues based on the comparison of the user model to the one or more foot statistical shape models, wherein the one or more corrective features comprise a microstructure having a size and position configured to address the one more issues; and
        generate a custom footwear model comprising the one or more determined corrective features, wherein a footwear part is created layer by layer based on the custom footwear model using additive manufacturing.

8. The apparatus of claim 7, wherein the user data includes one or more of: foot pressure data, gait data, body data, or image data.

9. The apparatus of claim 7, wherein the footwear part is one of an insole, a midsole, or an outsole.

10. The apparatus of claim 7, wherein the footwear part comprises the microstructure.

11. The apparatus of claim 7, wherein the footwear part is configured to alter a biomechanical action of the user's foot.

12. The apparatus of claim 7, wherein the footwear part is configured to improve a static weight distribution of a user's foot.

* * * * *